United States Patent [19]
Lee

[11] Patent Number: 6,010,857
[45] Date of Patent: *Jan. 4, 2000

[54] **DETECTION OF CERVICAL *CHLAMYDIA TRACHOMATIS* INFECTION**

[75] Inventor: Helen H Lee, Lake Forest, Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/060,663

[22] Filed: Apr. 15, 1998

Related U.S. Application Data

[63] Continuation of application No. 08/438,218, May 9, 1995, abandoned.

[51] Int. Cl.⁷ .............................. C12Q 1/68; C12P 19/34
[52] U.S. Cl. ............................ 435/6; 435/91.2; 435/91.5
[58] Field of Search ............................ 435/6, 91.2, 91.5; 536/24.32, 24.33

[56] References Cited

PUBLICATIONS

Chernesky et al. Tenth International Meeting of the International Society for STD Research (Helsinki Finland), Paper No. 80, Aug. 1993.

Chernesky. Journal of Clinical Microbiology. 32:2628–2685, Nov. 1994.

Lee et al. Lancet. 345: 213–216, Jan. 1995.

Bassiri et al. Journal of Clinical Microbiology. 33:898–900, Apr. 1995.

*Primary Examiner*—Carla J. Myers
*Attorney, Agent, or Firm*—Paul D. Yasger

[57] ABSTRACT

The present invention provides methods for detecting *Chlamydia trachomatis* infections using a female urine sample.

8 Claims, No Drawings

DETECTION OF CERVICAL *CHLAMYDIA TRACHOMATIS* INFECTION

This is a continuation of U.S. patent application Ser. No. 08/438,218, filed May 9, 1995 now abandoned.

FIELD OF THE INVENTION

The invention relates to detecting *Chlamydia trachomatis*. In particular, the invention relates to detecting *Chlamydia trachomatis* infections of cervical origin using a female urine sample.

BACKGROUND OF THE INVENTION

*Chlamydia trachomatis* (*C. trachomatis*) has been reported as the most common sexually transmitted disease in industrial societies and causes genital infections in both men and women. In the event *C. trachomatis* infections are undetected and untreated, the infection may escalate to sexually acquired reactive arthritis in men, and tubal factor infertility in women. Accordingly, it is important that such infections are quickly diagnosed and treated.

In men, because *C. trachomatis* infections are typically manifested in the urethra, such infections can be detected effectively by assaying a male urine sample. In women, however, *C. trachomatis* infections can occur in the urethra, the cervix or both. While some women are dually infected, there is a substantial incidence of infection of either the urethra or the cervix. *C. trachomatis* infections of the female urethra have been detected using a urine sample. However, detection of cervical *C. trachomatis* has typically required cervical swabbing, which is an invasive, expensive and uncomfortable procedure.

Inability to detect cervical *C. trachomatis* infections using a female urine sample is well documented. Thus, there remains a need for a rapid, specific and reproducible technique that is able to detect a cervical chlamydia infection using a female urine sample.

SUMMARY OF THE INVENTION

The present invention provides a method for detecting a cervical *C. trachomatis* infection by detecting the presence of *C. trachomatis* nucleic acid in a female urine sample. Additionally, the invention provides a method for simultaneously detecting a cervical and urethral *C. trachomatis* infection using a female urine sample. In either case, the method generally comprises contacting a female urine sample suspected of containing *C. trachomatis* nucleic acid with amplification reagents such as oligonucleotide probes and an enzyme having ligase activity. The resulting reaction mixture can then be placed under hybridization conditions to produce at least one copy of a *C. trachomatis* target sequence which is a nucleic acid sequence which is part of the *C. trachomatis* nucleic acid. *C. trachomatis* target sequences which are amplified can then be detected as an indication of a cervical *C. trachomatis* infection in instances where the urine sample is taken from a female subject having a cervical *C. trachomatis* infection. In addition to the oligonucleotide probes and enzyme having ligase activity, the amplification reagents preferably also include an enzyme having polymerase activity and at least one, but less than four of the deoxynucleotide triphosphates.

DETAILED DESCRIPTION OF THE INVENTION

Provided herein is a method of detecting *C. trachomatis* infections of cervical origin using a female urine sample. Preferably, the urine sample is taken from female first void urine (FVU). FVU refers to the first 40 mL of urine from a female urine stream, more typically FVU is the first 30 mL of urine from a female urine stream. It is noteworthy that the FVU can be taken from any micturition and a micturition from one time of day is not preferred over a micturition from another time of day.

The FVU, or an aliquot thereof, can be employed according to the present method. Generally, between about 1 mL and about 10 mL of the FVU is used, preferably between about 1 mL and about 5 mL of FVU is employed according to the instant method. The FVU, or FVU aliquot, can be treated to release nucleic acid from any *C. trachomatis* cells which may be contained therein. Cells can be lysed to release nucleic acid sequences using any of the methods well known in the art such as, for example, chemical methods, temperature methods and mechanical methods. Chemical methods for lysing cells include, but are not limited to contacting cells with a buffer that contains a lysing agent such as a detergent. Mechanical methods for lysing cells may include sonication and bead beating which is a procedure whereby small particulate material, such as glass beads, is combined with a cell sample and shaken. Various temperature treatments are also suitable for lysing cells. For example, heating a cell sample can be employed to lyse cells or alternate cycles of freezing and thawing a cell sample can be employed to lyse cells.

According to a preferred embodiment, prior to lysing any *C. trachomatis* cells, the cells preferably are purified, concentrated or otherwise separated from an FVU sample to remove enzyme inhibitors which may be present in the test sample. Separation of *C. trachomatis* cells from an FVU sample can be achieved through, for example, filtration or centrifugation.

Any of the methods for amplifying nucleic acid which are well known in the art are suitable for amplification of *C. trachomatis* nucleic acid which may be present in female urine. Such methods may include but are not limited to the polymerase chain reaction (PCR) which has been described in U.S. Pat. Nos. 4,683,195 and 4,683,202, the ligase chain reaction (LCR) described in EP-A-320 308, gap LCR (GLCR) described in European Patent Application EP-A439 182, and multiplex LCR described in International Patent Application No. WO 93/20227. These reactions typically employ "primers" (also referred to as "probes") to repeatedly generate copies of a target nucleic acid sequence which is usually a small region of a much larger nucleic acid sequence. Primers and probes are themselves nucleic acid sequences that are complementary to regions of a target sequence or a target sequence and its complement. Under suitable conditions, primers hybridize or bind to the complementary regions of the target sequence such that amplification product generated therefrom are copies of the target or its complement.

Copies of the target sequence are typically generated by the process of primer extension and/or ligation which utilizes enzymes with polymerase or ligase activity, separately or in combination, to add nucleotides to the hybridized primers and/or ligate adjacent primer pairs. While enzymatic methods of polymerization and ligation are predominant, other methods such as, for example, chemical polymerization and ligation are equally suitable for use according to the present invention. Nucleotides that are added to the primers or probes, as monomers or preformed oligomers, are also complementary to the target sequence. Once the primers or probes have been sufficiently extended and/or ligated they are separated from the target sequence, usually by heating the reaction mixture to a "melt temperature" which is one where complementary nucleic acid strands dissociate. Thus, a sequence complementary to the target sequence is formed.

A new amplification cycle can then take place to further amplify the number of target sequences by separating any double stranded sequences, allowing primers to hybridize to their respective targets, extending and/or ligating the hybridized primers and re-separating. The complementary sequences that are generated by amplification cycles can serve as templates for primer or probe extension to further amplify the number of target sequences. Hence, multiple copies of the target sequence and its complementary sequence are produced.

Generally, two primers which are complementary to a portion of a target strand and its complement are employed in PCR. For LCR, four primers, two of which are complementary to a target sequence and two of which are similarly complementary to the targets complement, are generally employed. Other reagents employed in amplification reactions are well known and include: enzyme cofactors such as magnesium; salts; nicotinamide adenine dinucleotide (NAD); and deoxynucleotide triphosphates (dNTPs) such as for example adenine triphosphate, guanine triphosphate, cytosine triphosphate and thymine triphosphate.

In addition to the enzymatic thermal amplifications described above, isothermal enzymatic amplification reactions could also be employed to amplify *C. trachomatis* nucleic acid which may be present in female urine. For example, "3SR" (Self-Sustained Sequence Replication) described in Fahy, E., et. al., *PCR Methods and Applications*, 1:

25–33(1991) and "SDA" (Strand Displacement Amplification) described in Walker, G. T., et. al., *PNAS* 89: 392–396 (1992) are amplification reactions which are similar to PCR, and with modifications, could be employed in the present method. Such modifications to the means for performing these reactions are detailed in the literature and are well known to those skilled in the art. For example, the use of avian myeloblastosis virus (AMV) reverse transcriptase (RT), *E. coli* RNase H and T7 RNA polymerase as well as ribonucleotide triphosphates (rNTPs) can be employed for 3SR in place of the enzyme and dNTPs employed in PCR. Similarly, *E. coli* DNA polymerase I (exo-Klenow polymerase) instead of, for example, Taq polymerase, a restriction enzyme such as HincII and deoxy-adenosine 5'-[a-thio]triphosphate can be employed in SDA.

In a particularly preferred embodiment, a modified form of LCR is employed as the means for amplifying nucleic acid. The modified LCR uses two pairs of probes herein designated A, B (primary probes), and A', B' (secondary probes). A' is substantially complementary to A, and B' is substantially complementary to B. Because of the antiparallel nature of DNA, probes A and B' are referred to herein as "upstream" probes, having their 3' end proximate their partners B and A', respectively; while probes B and A' are "downstream". At least one probe of one of the probe pairs initially includes a "modified" end which renders the hybridized probes "nonblunt" and/or not a suitable substrate for the ligase catalyzed fusion of the two probe duplexes. A "modified end" is defined with respect to the point of ligation rather than with respect to its complementary probe. Although other "modified ends" are known and within the scope of this invention, all "modified ends" described herein have omitted bases to create a "gap" between upstream and downstream probes when the probe pair is annealed to a target sequence. The presence of these modified ends reduces the falsely positive signal created by blunt-end ligation of complementary probe duplexes to one another in the absence of target.

"Correction" of the modification is subsequently carried out to render the probes ligatable. As used herein "correction" refers to the process of rendering, in a target dependent manner, the two primary probes or the two secondary probes ligatable to their partners. Thus, only those probes hybridized to target, target complement or polynucleotide sequences generated therefrom are "corrected." "Correction" can be accomplished by several procedures, depending on the type of modified end used. Correction by gap filling is exemplified herein. This utilizes a template-dependent polymerase and the requisite dNTPs to extend the upstream probe until its terminus is adjacent the downstream probe. The requisite dNTP(s) is/are determined based upon the target sequence.

As used herein, "point of ligation" or "intended point of ligation" refers to a specific location between two probe partners that are to be ligated in a template-dependent manner. It is the site at which the "corrected" probe lies adjacent its partner in 3' hydroxyl-5' phosphate relationship. For each set of four LCR probes there are two "points of ligation", a point for the primary probe partners and a point for the secondary probe partners. In conventional LCR, the two points of ligation are opposite one another, thus forming blunt ended duplexes when the probe pairs hybridize to one another. In the modified LCR embodiment, the points of ligation are not opposite one another; but are displaced from one another by one or more bases by virtue of the gaps.

Each of the modified LCR embodiment probes comprises deoxyribonucleic acid (DNA) which may be routinely synthesized using conventional nucleotide phosphoramidite chemistry and the instruments available from Applied Biosystems, Inc., (Foster City, Calif.); DuPont, (Wilmington, Del.); or Milligen, (Bedford, Mass.). Phosphorylation of the 5' ends of the appropriate probes may be accomplished by a kinase or by commercial synthesis reagents, as is known in the art. It may also be desirable to utilize one or more ribonucleotide residues in a probe.

In general, the modified LCR embodiment comprises a denaturation step, then repeated steps of (a) hybridizing the modified probes to the target (and, if double stranded so that target complement is present, to the target complement); (b) correcting the modification in a target dependent manner to render the probes ligatable; (c) ligating the corrected probe to its partner to form a fused or ligated product; and (d) dissociating the ligated product from the target and repeating the hybridization, correction and ligation steps to amplify the desired target sequence. Steps (a), (c) and (d) are essentially the same for all of LCR embodiments and can be discussed together. Step (b) will vary depending upon the type of modification employed.

Hybridization of probes to target (and optionally to target complement) is widely known in the art and is illustrated in EP-A-320 308. Probe length, probe concentration and stringency of conditions all affect the degree and rate at which hybridization will occur. Preferably, the probes are sufficiently long to provide the desired specificity; i.e., to avoid being hybridizable to nontarget sequences in the sample. Typically, probes on the order of 15 to 100 bases serve this purpose. Presently preferred are probes having a length of about 15 to about 40 bases.

The probes are added in approximately equimolar concentration since they are expected to react stoichiometrically. Each probe is generally present in a concentration ranging from about 5 nanomolar (nM) to about 90 nM; preferably from about 10 nM to about 35 nM. For a typical reaction volume of 200 μL, this is equivalent to adding from about $1.2\times10^{12}$ to about $4\times10^{12}$ molecules of each probe; and around $2\times10^{12}$ molecules per 200 μL has been a good starting point, however, reaction volumes may vary. The optimum quantity of probe used for each reaction also varies depending on the number of cycles which must be performed and the reaction volume. Probe concentrations can readily be determined by one of ordinary skill in this art to provide optimum signal for a given number of cycles.

"Hybridization" or "hybridizing" conditions is defined generally as conditions which promote annealing. It is well known in the art, however, that such annealing is dependent in a rather predictable manner on several parameters, including temperature, ionic strength, probe length and G:C content of the probes. For example, lowering the temperature of the reaction promotes annealing. For any given set of probes, melt temperature, or Tm, can be estimated by any of several known methods. Typically, diagnostic applications utilize hybridization temperatures which are slightly below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased probe length are also known to stabilize duplex formation because G:C pairings involve 3 hydrogen bonds where A:T pairs have just two, and because longer probes have more hydrogen bonds holding the probes together. Thus a high G:C content and longer probe lengths impact the "hybridization conditions" by elevating the melt temperature.

Once probes are selected for a given diagnostic application, the G:C content and length will be known and can be accounted for in determining appropriate "hybridization conditions". Since ionic strength is typically optimized for enzymatic activity, the only parameter left to vary is the temperature. For improved specificity, the hybridization temperature is selected slightly below the Tm of the probe; typically 2–10° C. below the Tm. Thus, obtaining suitable "hybridization conditions" for a particular probe set and system is well within ordinary skill of one practicing this art.

Following hybridization of the probes, the next step in the modified LCR embodiment is the specific correction step which creates "adjacent" probes, followed by the ligation of one probe to its adjacent partner. Thus, each corrected primary probe is ligated to its associated primary probe and each corrected secondary probe is ligated to its associated secondary probe. Correction may be accomplished using a DNA polymerase and most preferred is a thermostable DNA polymerase which obviates the need for adding additional polymerase for every cycle. The ligation of "adjacent" probes" generates "reorganized probes". Although enzymatic ligation is a preferred method of covalently attaching two adjacent probes, the term "ligation" will as used throughout the application should be understood to include any method of covalently attaching two probes. One alternative to enzymatic ligation is photo-ligation as described in EP-A-324 616.

The conditions and reagents which make possible the preferred enzymatic ligation step are generally known to those of ordinary skill in the art. Ligating reagents useful in the present invention include T4 ligase, and prokaryotic ligases such as *E. coli* DNA ligase, and *Thermus thermophilus* DNA ligase as taught in EP-320 308 and in EP-373 962. This latter ligase is presently preferred for its ability to maintain activity during the thermal cycling of LCR. Absent a thermally stable ligase, the ligase must be added each time the cycle is repeated. Also useful are eukaryotic ligases, including DNA ligase of Drosophila, reported by Rabin, et al., *J. Biol. Chem.* 261:10637–10647 (1986).

Once ligated, the ligated (reorganized) probe is dissociated (e.g. melted) from the target and, as with conventional LCR, the process is repeated for several cycles. The number of repeat cycles may vary from 1 to about 100, although from about 15 to about 70 are preferred.

It is desirable to design probes so that when hybridized to their complementary (secondary) probes, the ends away from the point of intended ligation are not able themselves to participate in other unwanted ligation reactions. Thus, ligatable sticky or blunt ends should be avoided. If such ends must be used, then 5' terminal phosphates should be avoided, eliminated or blocked. This can be accomplished either through synthesizing oligonucleotide probes (which normally carry no 5' terminal phosphate groups), or through the use of phosphatase enzymes to remove terminal phosphates (e.g. from oligonucleotides generated through restriction digests of DNA). Alternatively, ligation of the "wrong" outside ends of the probes can be prevented by blocking the end of at least one of the probes with a "hook" or marker moiety as will be described in detail below.

It should be appreciated that the use of four probes, as described above, produces the greatest amplification since the ligated or reorganized probes themselves can serve as target-equivalent templates in further cycles, thus resulting in exponential amplification. However, it is also possible to use just two probes extended and ligated on a single strand, such as is described in U.S. Pat. No. 5,185,243, as a detection method. Repeated steps of this nature will result (in the absence of the complementary probes) in a linear amplification. One skilled in the art can easily select the appropriate probe pairs from the probe sets (e.g. probes A and B; or probes B' and A') for ligation pairs.

Methods of detecting amplified sequences are well known in the art. Unlabeled probes can be detected following separation on a gel on the basis of weight or length, and staining with a suitable dye as is known in the art Detection can also be performed after separation of free labeled probe from labeled ligation or polymerization products, by determining the amount of label in one of the separated fractions. Separation may be accomplished by electrophoresis, by chromatography, including immunochromatography, by filtration, by the preferred specific ligand capture method described below, or by a combination of these methods. One method of detecting PCR amplified sequences has been described in European Patent Application No. 0 237 362. The labeled probe(s) contains a reporter group or label that is directly or indirectly capable of detection. Direct labels include chromogens, catalysts such as enzymes, fluorescent compounds, luminescent compounds, chemiluminescent compounds, and radioactive elements such as $^{32}P$ or $^{3}H$. Indirect labels include specific binding ligands as described below.

With respect to the modified LCR embodiment, a particularly preferred detection configuration employs haptens or "hooks" which are attached as reporter groups at the available outside ends of at least two probes (opposite ends of fused product), and preferably to the outside ends of all four probes. A "hook" is any ligand or moiety having an affinity to a binding partner. Typically, the hook(s) at one end of the fused product (e.g. the 5' end of first upstream probe A and the 3' end of second downstream probe A') comprises an antigen or hapten capable of being immobilized by a specific binding reagent (such as antibody or avidin) coated onto a solid phase. The hook(s) at the other end (e.g. the 3' end of first downstream probe B and the 5' end of second upstream probe B') contains a different antigen or hapten capable of being recognized by a label or a label system such as an antibody-enzyme conjugate.

Exemplary hooks include but are not limited to haptens (such as those described below) complementary polynucleotide "tail" regions, lectin/carbohydrate pairs, enzymes and their co-factors, and others known in the art.

Many different haptens are known in the art, and virtually any hapten can be used with the present invention, provided it does not interfere with hybridization or ligation. Some illustrative haptens include many drugs (e.g. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in co-pending, co-owned patent applications U.S. Ser. No. 07/808,508 now abandoned (adamantaneacetic acids), U.S. Ser. No. 07/808,839 now abandoned (carbazoles and dibenzofurans), both filed Dec. 17, 1991; U.S. Ser. No. 07/858,929 now abandoned (acridines), and U.S. Ser. No. 07/858,820 now abandoned (quinolines), both filed Mar. 27, 1992. The entire disclosure of each of the above-mentioned previously filed hapten applications is incorporated herein by reference.

Many methods of adding haptens to probes are known in the literature. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. No. 625,566, filed Dec. 11, 1990 now abandoned and Ser. No. 630,908, filed Dec. 20, 1990 U.S. Pat. No. 5,290,925 teach methods for labeling probes at their 5' and 3' termini, respectively. Both the aforementioned copending applications are incorporated by reference.

Publications WO92/10505, published Jun. 25, 1992 and WO 92/11388 published Jul. 9, 1992 teach methods for labeling probes at their 5' and 3' ends respectively. According to one known method for labeling an oligonucleotide, a label-phosphoramidite reagent is prepared and used to add the label to the oligonucleotide during its synthesis. For example, see Thuong, N. T. et al., *Tet. Letters,* 29(46) :5905–5908 (1988); or Cohen, J.S. et al., published U.S. patent application Ser. No. 07/246,688 now abandoned (NTIS ORDER No. PAT-APPL-7-246,688) (1989).

Thus, exemplary ligated oligonucleotides may have a carbazole at one end and an adamantane at the other end for the detection by the IMx® instrument (Abbott Laboratories, Abbott Park, Ill.) using the microparticle enzyme immunoassay (MEIA) technology. The assay protocol is similar to that used in the commercially available alpha-fetoprotein assay, with the following adaptations: (1) the anti-alpha-fetoprotein antibody coated microparticles are replaced with anti-carbazole antibody coated microparticles; and (2) the conjugates of anti-alpha fetoprotein antibodies:alkaline phosphatase are replaced with the conjugates of anti-3-phenyl-1-adamantaneacetic acid antibodies:alkaline phosphatase.

Protocols for Microparticle Enzyme ImmunoAssays (MEIAs), such as are performed on the Abbott IMx® instrument are further described in EP-A-439,182, in EP-A-288 793 and in Fiore, M. et al *Clin. Chem.,* 34/9:1726–1732 (1988). An exemplary protocol is as follows. 100 μL of the sample which has been amplified by LCR is pipetted into the sample well. 30–50 μL of this sample is then pipetted into the incubation well, the anticarbazole antibody coated microparticles are added to the well. An appropriate period of incubation follows which allows the formation of a complex consisting of anticarbazole antibodies and carbazole labeled nucleic acid sequences. After the incubation, the mixture is pipetted onto the glass fiber capture matrix of the IMx® reaction cell, and antiadamantane antibodies conjugated to alkaline phosphatase are added. This leads to a microparticle-oligonucleotide-enzyme complex which is captured by the glass fiber capture matrix. After the removal of excess reagent in a wash step (throughout this protocol, the blotter beneath the glass fiber capture matrix absorbs reagent solutions which would otherwise overflow the glass fiber capture matrix), the glass-fiber capture matrix is treated with 4-methylumbelliferyl phosphate (MUP). The surface-bound enzyme converts the nonfluorogenic MUP to 4-methylumbelliferone (MU), whose fluorescence can be measured. The numerical IMx rate values given in the following examples represent the rate of formation of fluorescent product, expressed in counts/sec/sec (c/s/s). The amount of ligated probe is directly related to this rate. It should be noted that the IMx® instrument typically generates "machine" noise or background in the range of 2–12 c/s/s.

In the illustrative examples which follow, probe pairs are labeled with a fluorescein hapten and a biotin hapten or with a carbazole hapten and an adamantaneacetic acid (adamantane) hapten. Typically, fluorescein and biotin are used together and adamantane and carbazole are used together in accordance with the description above although any combination of virtually any haptens would be possible. Preferably, each member of a probe pair has a different label.

Other equally suitable methods of detection useful in the practice of the present invention include ELISA, EIA, immunochromatography, and nucleic acid hybridization techniques including southern blotting, dot blotting, slot blotting, solution hybridization and others well known in the art.

Quantities of polymerase are expressed in units, defined as follows: 1 unit of enzyme equals the amount of enzyme required to incorporate 10 nanomoles total nucleotides into acid-insoluble material in 30 min at 70° C. Units of ligase enzyme are defined herein as: 1 mg of 95% purified *Thermus thermophilus* DNA ligase has a specific activity of about $1 \times 10^8$ units. While this is not precisely standardized and may vary by as much as 20%, optimization is within the skill of the routine practitioner.

For purposes of this invention, the target sequence is described to be single stranded. However, this should be understood to include the case where the target is actually double stranded but is simply separated from its complement prior to hybridization with the probes. In the case of double stranded target, the third and fourth (secondary) probes, A' and B', respectively, will participate in the initial step by hybridizing to the target complement. In the case of single stranded target, they will not participate in the initial hybridization step, but will participate in subsequent hybridization steps, combining with the primary fused sequence produced by ligating the first and second probes. Target sequences may comprise deoxyribonucleic acid (DNA) or ribonucleic acid (RNA), although the targets shown and claimed herein are DNA. Also for the purposes of the present invention deoxynucleotide triphosphates include: deoxyadenosine triphosphate; deoxythymidine triphosphate; deoxyguanosine triphosphate; and deoxycytosine triphosphate. However, this is not meant to exclude modified bases or nontraditional bases that are analogs of these four if they can form hydrogen bonds in an analogous manner. Moreover, the term "analogs" is intended to encompass modification in or substitution of the backbone linking traditional or nontraditional bases. Such backbone modifications include, but are not limited to peptide linkages between bases which are described in PCT Patent Application No. WO 92/20703 and morpholino linkages between bases which are described in U.S. Pat. No. 5,034,506.

Oligonucleotide sequences (SEQ ID NOS. 1–15) (FIG. 1) used to exemplify the invention are derived from the gene coding for the major outer membrane protein (MOMP) of *Chlamydia trachomatis* as described by Baehr, W. et al., *Proc. Nat'l. Acad. Sci. (USA)*, 85,4000–4004 (1988). The gene is at least 1120 nucleotides long and is typically present in one copy per organism. Other oligonucleotides corresponding to (SEQ ID NOS. 16–25) (FIG. 2) of the present invention were derived from a cryptic plasmid found in *Chlamydia trachomatis* (Hatt, C., et al., *Nucl. Acids Res.* 16 (9):4053–4067). The cryptic plasmid, typically present in 7–10 copies per organism, is 7498 base pairs in length and contains several open reading frames.

The invention will now be described further by way of examples which are illustrative of the invention and are not intended to limit it in any way. For example, sequences of specific length are listed. It should be understood that sequences covering the same map positions but having slightly fewer or greater numbers of bases are deemed to be equivalents of these sequences and fall within the scope of the invention, provided they will hybridize to the same positions on the target as the listed sequences. It is also understood that sequences having homology to the target sequences of about 80% or more also fall within the scope of the present invention. Preferably any base substitutions in the LCR sequences of the present invention lie 3 or more nucleotides away from the gaps or recesses.

Because Chlamydia is an obligate intracellular parasite, it is difficult to quantify control dilutions with accuracy. Although one elementary body (EB) and one inclusion forming unit (IFU) are theoretically equivalent to one organism, this equality is rarely the case in practice. When non-viable organisms are present in the same EB or IFU, the count of actual organisms is inaccurate. Control solution IFUs are estimated by their IMx® rate using a standard curve calibrated against stock solutions cultured out to estimate EBs or IFUs.

EXAMPLE 1

Detection of *Chlamydia trachomatis* Using Probe Set 1 (SEQ ID NOS. 2–5)

Oligonucleotide probes were chosen to detect a target sequence corresponding to nucleotides 435–482 of the MOMP gene (SEQ ID NO. 1) of *Chlamydia trachomatis*. Probe set 1 (SEQ ID NOS. 2–5) was tested against panel of organisms consisting of a wide variety of *Chlamydia trachomatis* serovars (serological variants), for its ability to detect target DNA from these organisms. LCR reaction mixtures contained LCR buffer (50 mM EPPS, 30 mM MgCl$_2$, 20 mM K$^+$ [from KOH and KCl], 10 µM NAD), 1.7 µM dATP, 1.7 µM dCTP (gap-filling nucleotides) 8×10$^{11}$ molecules of each oligonucleotide probe labeled with carbazole and adamantane as described above, 5 µg/ml acetylated bovine serum albumin (BSA), 0.5 mM EDTA, 0.02% by weight sodium azide, 2 units Thermus sp. DNA polymerase (Molecular Biology Resources, Milwaukee, Wis.) 18,000 units *Thermus thermophilus* DNA ligase (Abbott Laboratories), and target DNA (equivalent to 10 elementary bodies of *Chlamydia trachomatis*), all in a total volume of 200 µl. Cycling was then performed on a Perkin-Elmer Model 480 thermocycler at the following settings: 97° C., 1 sec; 55° C., 1 sec; 62° C., 50 sec; for a total of 40 cycles.

Target DNA may be prepared by a variety of methods well known in the art In the present example, target DNA was prepared by heating the organism (grown in McCoy cells) at 85° C.–95° C. for 10 minutes in a buffer consisting of 5 mM EPPS, 60 mM MgCl$_2$.

Following amplification, ligation products were detected using a sandwich immunoassay using an Abbott automated IMx® Analyzer as described above. Table 1 shows the results of the assay expressed as counts/sec/sec (c/s/s).

TABLE 1

| Target DNA | IMx ® Rate (c/s/s) |
|---|---|
| *C. trachomatis* serovar | |
| A | 1370 |
| B | 1076 |
| Ba | 495 |
| C | 487 |
| D | 1022 |
| E | 575 |
| F | 1140 |
| G | 527 |
| H | 458 |
| I | 640 |
| J | 724 |
| K | 1058 |
| L1 | 930 |
| L2 | 1309 |
| L3 | 1077 |
| Negative Control (330 ng salmon sperm DNA) | 14 |

These results show that probe set 1 (SEQ ID NOS 2–5) was capable of detecting target DNA from 15 different serovars of *Chlamydia trachomatis*.

EXAMPLE 2

Detection of Target DNA from Microbial Sources Using Probe Set 1 (SEQ ID NOS. 2–5)

Probe set 1 (SEQ ID NOS. 2–5) was used in LCR assays against a panel of target DNAs derived from several microbial sources. LCR was performed as described in Example 1 except that target DNA was extracted from the bacterial sources and was present in the reactions at about 10$^5$ copies per reaction. Probes were labeled with carbazole and adamantane as shown in FIG. 1 as described above, and were provided at 7×10$^{11}$ molecules/200 µL reaction. The analysis was carried out in several runs on the IMx® instrument and the positive control (PC) and negative control (NC) values for each run are provided. The positive control in each run was estimated to be 5.0 IFUs of Chlamydia; the negative control was 330 ng salmon sperm DNA.

Table 2 shows the results of the assays.

TABLE 2

| Run | Target Organism | IMx ® Rate (c/s/s) | PC & NC Values | |
|---|---|---|---|---|
| A | Neisseria sicca | 162 | | |
| A | N. flavescens | 16 | | |
| A | N. perflava | 63 | PC | 1265 |
| A | N. subflava | 208 | NC | 12 |
| A | N. flava | 20 | | |
| A | N. catarrhalis | 15 | | |
| B | N. mucosa | 76 | | |
| B | N. cinerea | 15 | | |
| B | N. polysacchareae | 82 | PC | 1254 |
| B | N. elongata | 34 | NC | 12 |
| B | N. lactamica | 51 | | |
| C | N. gonorrhoeae | 16 | | |
| C | N. meningitidis | 84 | | |
| C | Morganella morganii | 89 | PC | 1252 |
| C | Escherichia coli | 15 | NC | 66 |
| C | Pseudomonas aeruginosa | 15 | | |
| D | Enterobacter aerogenes | 15 | | |
| D | Acinetobacter calcoaceticus | 16 | | |
| D | Corynebacterium hoffmanni | 26 | PC | 1283 |
| D | Yersinia enterocolitica | 14 | NC | 12 |
| D | Alcaligenes faecalis | 115 | | |
| D | Proteus vulgaris | 15 | | |
| E | Staphylococcus aureus | 17 | | |
| E | Serratia marcescens | 36 | PC | 1338 |
| E | Staphylococcus epidermidis | 64 | NC | 16 |
| E | Bacillus subtilis | 16 | | |
| F | Klebsiella pneumoniae | 34 | | |
| F | Salmonella enteritidis | 87 | | |
| F | Providencia stuartii | 15 | PC | 1112 |
| F | Enterobacter cloacae | 51 | NC | 14 |
| F | Shigella sonnei | 15 | | |
| F | Mima polymorpha | 63 | | |
| G | Hemophilus influenzae | 16 | | |
| G | Herella vagincola | 156 | | |
| G | Streptococcus pyogenes | 24 | PC | 1266 |
| G | Streptococcus faecalis | 15 | NC | 13 |
| G | Lactobacillus plantarum | 98 | | |
| H | Salmonella minnesota | 16 | | |
| H | Hemophilus parainfluenzae | 49 | PC | 1238 |
| H | Aeromonas hydrophila | 16 | NC | 13 |
| H | Corynebacterium sp. | 14 | | |
| I | Veillonella sp. | 110 | | |
| I | Moraxella osloensis | 189 | PC | 1226 |
| I | Trichomonas vaginalis | 57 | NC | 14 |
| I | Gardnerella vaginalis | 34 | | |

The results show that probe set 1 gave relatively little detectable signal when tested with target DNA from a variety of microbial sources using LCR, when compared with the signal generated with DNA from *Chlamydia trachomatis*. Although signal from some bacterial species was greater than background, none were even ⅙ the signal from the Chlamydia positive control.

EXAMPLE 3
Detection of *Chlamydia trachomatis* With Probe Set 4 (SEQ ID NOS. 17–20)

Probe set 4 (SEQ ID NOS. 17, 18, 19, and 20) (FIG. 2) was used to detect a target DNA corresponding to oligonucleotides 6917–6964 (SEQ ID NO. 16) of the *Chlamydia trachomatis* cryptic plasmid described above. Reactions were performed as described in Example 1 except that the gap-filling nucleotides were dCTP and dTTP, 1.2 units of Thermus sp DNA polymerase was used and 10,800 units of Thermus thermophilus DNA ligase was used. Probes were provided at $6.2 \times 10^{11}$ molecules/200 µL reaction and cycling was performed at 97° C. for 1 sec., 55° C. for 1 sec., and 62° C. for 50 sec., for a total of 40 cycles. Ligation products were analyzed on an automated IMx® analyzer as described in Example 1 and results are shown in Table 3.

TABLE 3

| Target DNA | IMx ® rate (c/s/s) |
|---|---|
| *C. trachomatis* serovar | |
| A | 988 |
| B | 871 |
| Ba | 715 |
| C | 721 |
| D | 713 |
| E | 649 |
| F | 747 |
| G | 673 |
| H | 513 |
| I | 601 |
| J | 698 |
| K | 692 |
| L1 | 693 |
| L2 | 801 |
| L3 | 839 |
| Negative Control (330 ng salmon sperm DNA) | 13 |

These results show that probe set 4 (SEQ ID NOS. 17, 18, 19, and 20) was capable of detecting target DNA from all 15 of the *Chlamydia trachomatis* serovars tested.

EXAMPLE 4
Detection of Target DNA from Intact Microorganisms Using Probe Set 4 (SEQ ID NOS. 17–20)

In order to assess the specificity of probe set 4 (SEQ ID NOS. 17–20), LCR was performed using a wide variety of intact microorganisms including various bacteria, fungi, and viruses as well as strains of *Chlamydia pneumoniae* and *Chlamydia psittaci*. LCR was performed as described in Example 3 except that 2 units of Thermus sp DNA polymerase and 18,000 units of *Thermus thermophilus* DNA ligase were used. The analysis was carried out in several runs on the IMx® instrument and the probe concentrations and positive control (PC) and negative control (NC) values for each run are provided in Table 5, below.

Results are shown in Tables 4 (microorganisms) and 4A (Chlamydia species).

TABLE 4

| Run | Target (Quantity) Bacterial species (organisms/reaction): | IMx ® (c/s/s) |
|---|---|---|
| b | Acinetobacter calcoaceticus ($1.2 \times 10^7$) | 11 |
| m | Actinomyces israelii ($9.2 \times 10^7$) | 11 |
| b | Aeromonas hydrophila ($1.0 \times 10^8$) | 10 |
| b | Alcaligenes faecalis ($5.0 \times 10^7$) | 13 |
| b | Bacillus subtilis ($6.0 \times 10^7$) | 10 |
| b | Bacillus thuringiensis ($3.0 \times 10^7$) | 10 |
| b | Bacteroides fragilis ($2.0 \times 10^7$) | 10 |
| b | Bifobacterium longum ($1.5 \times 10^7$) | 9 |
| a | Branhamella catarrhalis ($1.8 \times 10^8$) | 12 |
| c | Citrobacter freundii ($3.1 \times 10^8$) | 14 |
| m | Clostridium sporogenes ($7.8 \times 10^7$) | 24 |
| c | Corynebacterium renale ($2.0 \times 10^8$) | 10 |
| c | Edwardsiella tarda ($1.4 \times 10^8$) | 10 |
| c | Enterobacter cloacae ($3.0 \times 10^7$) | 13 |
| c | Enterobacter aerogenes ($1.8 \times 10^8$) | 23 |
| d | Enterococcus faecalis ($6.0 \times 10^7$) | 12 |
| d | Enterococcus faecium ($2.6 \times 10^8$) | 13 |
| d | Escherichia coli ($8.0 \times 10^7$) | 19 |
| d | Ewingella americana ($1.0 \times 10^8$) | 23 |
| d | Flavobacterium odoratum ($1.0 \times 10^8$) | 12 |
| d | Fusobacterium nucleatum ($2.0 \times 10^8$) | 12 |
| d | Gardnerella vaginalis ($2.0 \times 10^7$) | 24 |
| d | Hafnia alvei ($6.0 \times 10^8$) | 17 |
| n | Helicobacter pylori ($1.0 \times 10^5$) | 11 |

TABLE 4-continued

| Run | Target (Quantity) Bacterial species (organisms/reaction): | IMx ® (c/s/s) |
|---|---|---|
| e | Hemophilus influenzae ($3.0 \times 10^7$) | 15 |
| l | Hemophilus ducreyi ($3.0 \times 10^6$) | 11 |
| e | Klebsiella pneumoniae ($7.0 \times 10^7$) | 11 |
| e | Lactobacillus casei ($1.0 \times 10^8$) | 9 |
| e | Morganella morganii ($3.0 \times 10^7$) | 12 |
| l | Moraxella lacunata ($3.4 \times 10^7$) | 11 |
| l | Mycobacterium tuberculosis RaH37 ($1.0 \times 10^7$) | 27 |
| a | Mycobacterium avium ($4.0 \times 10^9$) | 10 |
| a | Mycobacterium gordonae ($5.0 \times 10^8$) | 11 |
| e | Neisseria gonorrheae ($4.0 \times 10^7$) | 11 |
| e | Neisseria lactamica ($3.0 \times 10^7$) | 16 |
| e | Neisseria meningitidis ($2.0 \times 10^7$) | 10 |
| e | Neisseria sicca ($2.0 \times 10^7$) | 10 |
| f | Pasteurella multocida ($1.0 \times 10^8$) | 18 |
| f | Peptostrept. asaccharolyticus ($2.0 \times 10^7$) | 14 |
| f | Pleisiomonas shigelloides ($7.0 \times 10^7$) | 16 |
| f | Proteus mirabilis ($4.0 \times 10^7$) | 17 |
| f | Proteus vulgaris ($3.0 \times 10^8$) | 17 |
| f | Propionibacterium acnes ($2.0 \times 10^7$) | 11 |
| f | Providencia stuartii ($2.8 \times 10^8$) | 10 |
| f | Pseudomonas aeruginosa ($8.0 \times 10^8$) | 15 |
| g | Salmonella enteritidis ($2.7 \times 10^8$) | 22 |
| g | Salmonella minnesota ($7.0 \times 10^7$) | 20 |
| g | Salmonella typhimurium ($4.0 \times 10^7$) | 19 |
| g | Shigella sonnei ($2.0 \times 10^8$) | 23 |
| o | Staphylococcus aureus ATCC6358 ($1.0 \times 10^7$) | 127 |
| g | Staphylococcus epidermidis ($2.5 \times 10^8$) | 14 |
| l | Streptococcus agalactiae ($1.2 \times 10^7$) | 10 |
| g | Streptococcus mitis ($1.3 \times 10^8$) | 12 |
| h | Streptococcus mutans ($1.1 \times 10^8$) | 10 |
| h | Streptococcus pneumoniae ($6.0 \times 10^7$) | 9 |
| h | Streptococcus pyogenes ($9.0 \times 10^7$) | 21 |
| l | Streptomyces griseus ($5.1 \times 10^7$) | 14 |
| h | Veillonella caviae ($3.0 \times 10^7$) | 10 |
| h | Vibrio parahemolyticus ($5.7 \times 10^8$) | 10 |
| h | Yersinia enterocoliticus ($4.0 \times 10^8$) | 23 |
| Yeast and Fungi species: | | |
| l | Blastomyces dermatidis (DNA, 0.5 ug) | 10 |
| b | Candida albicans ($9.0 \times 10^7$) | 9 |
| c | Candida albicans ($4.0 \times 10^7$) | 10 |
| c | Cryptococcus laurentii ($7.0 \times 10^7$) | 4 |
| l | Cryptococcus neoformans (DNA, 0.5 ug) | 10 |
| l | Histoplasma capsulatum (DNA, 0.5 ug) | 18 |
| g | Saccharomyces cerevisiae ($9.0 \times 10^7$) | 13 |
| Viruses: | | |
| i | Adenovirus ($1.0 \times 10^5$) | 11 |
| k | Cytomegaloviris 169 ($1.0 \times 10^5$) | 105 |
| k | Epstein-Barr virus ($1.0 \times 10^5$) | 10 |
| k | Hepatitis A & B virus ($1.0 \times 10^5$) | 90 |
| i | Herpes simplex virus I ($1.0 \times 10^5$) | 12 |
| i | Herpes simplex viras II ($1.0 \times 10^5$) | 12 |
| k | Human herpes virus 6 ($1.0 \times 10^5$) | 10 |
| i | HIV provirus ($1.0 \times 10^5$) | 12 |
| i | Human papilloma virus 16 ($1.0 \times 10^5$) | 11 |
| j | Human papilloma virus 18 ($1.0 \times 10^5$) | 21 |
| k | Varicella zoster ($1.0 \times 10^5$) | 10 |
| Parasites: | | |
| i | Treponema pallidum (DNA, $1.0 \times 10^5$) | 11 |

TABLE 4A

| Run | Target | IMX ® Rate (c/s/s) | Result |
|---|---|---|---|
| Chlamydia pneumoniae strains: | | | |
| p | TWR 183 | 14 | (−) |
| p | AR 39 | 10 | (−) |
| p | AR 388 | 9 | (−) |
| p | CM 1 | 20 | (−) |
| p | CWL011 | 13 | (−) |

TABLE 4A-continued

| Run | Target | IMX ® Rate (c/s/s) | Result |
|---|---|---|---|
| q | BAL 15 | 98 | (−) |
| q | BAL 16 | 10 | (−) |
| q | BAL 37 | 10 | (−) |
| q | FM 16 | 16 | (−) |
| r | VR 1310 | 14 | (−) |
| r | VR 1356 (2023) | 192 | (−) |
| r | VR 1355 (2043) | 95 | (−) |
| r | 2364 | 13 | (−) |
| Chlamydia psittaci strains: | | | |
| p | SM006 | 15 | (−) |
| p | 6BC | 12 | (−) |

The probe concentrations used and the resulting positive control (PC) and negative control (NC) values for each run of Example 4 are given in Table 5. The positive control was estimated to be 5.0 IFUs of *Chlamydia trachomatis* and the negative control was 330 ng salmon sperm DNA in each run.

TABLE 5

| Run | Probe Concentration | PC Value | NC Value |
|---|---|---|---|
| a | $6.0 \times 10^{11}$ molecules/reaction | 1704 | 10 |
| b | $6.0 \times 10^{11}$ molecules/reaction | 1436 | 9 |
| c | $6.0 \times 10^{11}$ molecules/reaction | 1514 | 9 |
| d | $6.0 \times 10^{11}$ molecules/reaction | 1246 | 11 |
| e | $6.0 \times 10^{11}$ molecules/reaction | 1024 | 9 |
| f | $6.0 \times 10^{11}$ molecules/reaction | 1166 | 9 |
| g | $6.0 \times 10^{11}$ molecules/reaction | 1970 | 12 |
| h | $6.0 \times 10^{11}$ molecules/reaction | 1323 | 9 |
| i | $6.0 \times 10^{11}$ molecules/reaction | 1401 | 10 |
| j | $6.0 \times 10^{11}$ molecules/reaction | 1409 | 11 |
| k | $6.0 \times 10^{11}$ molecules/reaction | 1223 | 9 |
| l | $4.6 \times 10^{11}$ molecules/reaction | 1756 | 10 |
| m | $4.6 \times 10^{11}$ molecules/reaction | 1412 | 10 |
| n | $6.0 \times 10^{11}$ molecules/reaction | 1223 | 9 |
| o | $5.0 \times 10^{11}$ molecules/reaction | 1951 | 11 |
| p | $5.0 \times 10^{11}$ molecules/reaction | 1575 | 10 |
| q | $5.0 \times 10^{11}$ molecules/reaction | 1851 | 10 |
| r | $5.0 \times 10^{11}$ molecules/reaction | 1888 | 10 |

These results show that probe set 4 (SEQ ID NOS. 17, 18, 19, and 20) produced ligation products only when *Chlamydia trachomatis* was present in the LCR reaction mixture and not when a wide variety of other microorganisms were present, including closely related *Chlamydia pneumoniae* and *Chlamydia psittaci* strains.

EXAMPLE 5

Detection of *Chlamydia trachomatis* With Probe Set 5 (SEQ ID NOS. 22–25)

Probe set 5 (SEQ ID NOS. 22–25) was used to detect a target DNA corresponding to nucleotides 6107–6160 (SEQ ID NO. 21) (FIG. 2) of the *Chlamydia trachomatis* cryptic plasmid described above. Reactions were conducted as described in Example 1 also using gap-filling nucleotides dATP and dCTP, but not acetylated BSA. Cycling was performed at 97° C. for 1 sec., 58° C. for 1 sec., and 65° C. for 20 secs. for a total of 37 cycles. Probes were labeled with biotin and fluorescein as described above, and provided at $2 \times 10^{12}$ molecules/200 μL reaction. Ligation products were analyzed on an IMx® analyzer as shown in FIG. 2 and as described above. Results are shown in Table 6.

TABLE 6

| Target DNA | IMx ® Rate (c/s/s) |
|---|---|
| C. trachomatis serovar | |
| A | 916 |
| B | 864 |
| Ba | 833 |
| C | 894 |
| D | 741 |
| E | 557 |
| F | 796 |
| G | 909 |
| H | 697 |
| I | 598 |
| J | 870 |
| K | 772 |
| L1 | 1211 |
| L2 | 1387 |
| L3 | 1390 |
| Negative Control (330 ng Human Placental DNA) | 86 |

These results show that probe set 5 (SEQ ID NOS. 22–25) is capable of detecting 15 different serovars of Chlamydia trachomatis.

EXAMPLE 6
Detection of Target DNA from Microbial Sources Using Probe Set 5 (SEQ ID NOS. 22–25)

The specificity of probe set 5 was assessed using target DNA from a series of non-chlamydial microorganisms. LCR was performed as described in Example 5 in four runs except that target DNA was present at about $10^5$ genomes/reaction. Positive Control (PC) was estimated to be 5.0 IFUs and Negative Control (NC) was 330 ng human placental DNA in each run. The PC and NC values for each run are shown in Table 7. IMx® analysis was performed as described above. Table 7 also shows the results of these assays.

TABLE 7

| Run | Organism | IMx ® Rate (c/s/s) | PC & NC Values | |
|---|---|---|---|---|
| A | Lactobacillus | 16 | | |
| A | Hemophilus ducreyi | 21 | PC | 2148 |
| A | Fusobacterium | 43 | NC | 11 |
| A | Yersinia | 10 | | |
| A | Corynebacterium | 18 | | |
| B | Hemophilus influenzae | 28 | | |
| B | Bacillus fragilis | 21 | | |
| B | Candida albicans | 23 | PC | 2228 |
| B | Klebsiella pneumoniae | 29 | NC | 22 |
| B | Gardnerella vaginalis | 26 | | |
| B | Staphylococcus epidermidis | 42 | | |
| C | Acinetobacter | 28 | | |
| C | Streptococcus faecalis | 9 | | |
| C | Pseudomonas | 20 | PC | 2018 |
| C | Proteus vulgaris | 10 | NC | 17 |
| C | Chlamydia psittaci | 11 | | |
| C | Escherichia coli | 9 | | |
| C | Neisseria gonorrhoeae | 14 | | |
| D | Neisseria meningitidis | 11 | PC | 2120 |
| | | | NC | 21 |

These results indicate that probe set 5 (SEQ ID NOS. 22–25) shows no cross reactivity with target DNA derived from a variety of non-chlamydial microorganisms or from Chlamydia psittici.

EXAMPLE 7
Detection of Chlamydia trachomatis Target DNA Using Probe Set 2 (SEQ ID NOS. 7–10)

Probe set 2 (SEQ ID NOS. 7–10) was used to detect target DNA corresponding to nucleotides 788–835 (SEQ ID NO. 6) of the MOMP gene of Chlamydia trachomatis. Probes were synthesized and labeled as shown in FIG. 1 and described above, and were provided at $2 \times 10^{12}$ molecules/ 200 µL reaction.

LCR assays were performed as described in Example 1 using dATP and dCTP as gap filling nucleotides. Table 8 shows the results of the assays.

TABLE 8

| Target DNA C. trachomatis Serovar | IMX ® Rate (c/s/s) |
|---|---|
| A | 11 |
| B | 32 |
| Ba | 21 |
| C | 24 |
| D | 182 |
| E | 11 |
| F | 232 |
| G | 83 |
| H | 26 |
| I | 9 |
| J | 11 |
| K | 44 |
| L1 | 220 |
| L2 | 218 |
| L3 | 9 |
| Negative Control (330 ng human placental DNA) | 30 |

These results show that probe set 2 yielded relatively low IMx® rates in most serovars tested. The best results were obtained for serovars D, F, L1, and L2.

EXAMPLE 8
Detection of Non-Chlamydia Target DNA Using Probe Set 2 (SEQ ID NOS. 7–10)

Probe set 2 was used at $2 \times 10^{12}$ molecules/ 200 µL reaction in LCR assays using target DNAs from a variety of non-chlamydial microorganisms. LCR was performed as described in Example 7 except that target DNA was present at about $10^8$ genomes per reaction. Positive Control (PC) was estimated to be 5.0 IFUs and Negative Control (NC) was 330 ng human placental DNA in each run. Results of these assays are shown in Table 9.

TABLE 9

| Run | Organism | IMx ® Rate (c/s/s) | PC & NC Values | |
|---|---|---|---|---|
| a | Neisseria sicca | 15 | | |
| a | Neisseria flavescens | 12 | | |
| a | Neisseria perflava | 11 | PC | 687 |
| a | Neisseria subflava | 11 | NC | 14 |
| a | Neisenia flava | 10 | | |
| a | Neisseria catarrhalis | 10 | | |
| b | Neisseria mucosa | 11 | | |
| b | Neisseria cinerea | 11 | | |
| b | Neisseria polysacchareae | 11 | PC | 640 |
| b | Neisseria elongata | 11 | NC | 13 |
| b | Neisseria lactamica | 11 | | |
| c | Neisseria meningitidis | 13 | | |
| c | Neisseria gonorrhoeae | 17 | | |
| c | Moraxella morganii | 12 | PC | 675 |
| c | Escherichia coli | 11 | NC | 15 |
| c | Pseudomonas aeruginosa | 11 | | |
| d | Enterobacter aerogenes | 13 | | |
| d | Acinetobacter calcoaceticus | 12 | | |
| d | Yersinia enterocoliticus | 10 | PC | 680 |

TABLE 9-continued

| Run | Organism | IMx ® Rate (c/s/s) | PC & NC Values |
|---|---|---|---|
| d | Alcaligenes faecalis | 10 | NC 13 |
| d | Proteus vulgaris | 10 | |

These results show that probe set 2 did not produce detectable ligation products when DNA from a variety of non-chlamydial bacteria were used as target DNA.

EXAMPLE 9
Detection of *Chlamydia trachomatis* Using Probe Set 3 (SEQ ID NOS. 12–15)

Probe set 3 (SEQ ID NOS. 12–15) was assessed for its ability to detect target DNA corresponding to nucleotides 1501–1506 of the MOMP gene in a variety of serovars of *Chlamydia trachomatis*. (FIG. 1). LCR was performed as described in Example 1 (using dATP and dCTP as filling nucleotides) except that cycling was performed as follows: 97° C., 1 sec; 58° C., 1 sec; 65° C., 10 sec; for a total of 37 cycles. Probes were used at $2 \times 10^{12}$ molecules/200 µL reaction. Results are shown in Table 10.

TABLE 10

| Target DNA C. trachomatis Serovar | IMx ® Rate (c/s/s) |
|---|---|
| A | 32 |
| B | 317 |
| Ba | 209 |
| C | 54 |
| D | 360 |
| E | 141 |
| F | 190 |
| G | 272 |
| H | 122 |
| I | 10 |
| J | 336 |
| K | 27 |
| L1 | 290 |
| L2 | 356 |
| L3 | 286 |
| Negative Control (330 ng human placental DNA) | 11 |

The results show that probe set 3 (SEQ ID NOS. 12–15) was capable of detecting target DNA from *Chlamydia trachomatis* serovars B, Ba, D, E, F, G, H, J, L1, L2 and L3, while target DNA from serovars A, C, I and K yielded little signal.

EXAMPLE 10
Detection of *Chlamydia trachomatis* in Female Urine with Probe Set 4 (SEQ ID NOS. 17–20)

The urine specimens assayed in this example were first void urine samples (first 20 mL of the urine stream) collected from 447 women. Each urine specimen was briefly vortexed and a 1.0 mL aliquot of the specimen was transferred to a 1.7 mL microcentrifuge tube and centrifuged for 10 minutes at 16,000×g. The supernatant was removed and the remaining pellet was resuspended in 1.0 mL of urine resuspension buffer available from Abbott Laboratories, Abbott Park, Ill. The resuspended pellet was heated at 95° C.–100° C. for 15 minutes and a 100 µL aliquot of each heat treated sample was used for assay by LCR. Probe set 4 (SEQ ID NOS. 17, 18, 19, and 20) was used to detect a target DNA corresponding to oligonucleotides 6917–6964 (SEQ ID NO. 16) of the *Chlamydia trachomatis* cryptic plasmid described above. LCR reactions were performed as described in Example 3.

Endocervical swab specimens were also taken from the women who donated first void urine specimens. These specimens were tested with conventional methods by inoculating the specimens onto McCoy cell monolayers in 96-well microculture plate with a blind passage and iodine staining essentially as described in Chernesky, M. A., et. al., *J. Infect. Dis.* 161: 124–126 (1990).

Also, the FVU samples were assayed with Chlamydiazyme® enzyme immunoassay (EIA) available from Abbott Laboratories.

Culture of the cervical swab samples yielded a positive result in 15 women, LCR yielded a positive result in 27 women and EIA of the FVU yielded a positive result in 10 women. Of the women who tested positive by culture, 14 of them also tested positive by LCR. The woman who tested positive by culture and negative by LCR was reassayed by the LCR method after her FVU sample was diluted 1:10 and 1:100. Both dilutions gave a positive result upon retesting. All of the women who tested positive by EIA also tested positive by LCR.

Based upon the foregoing results, the LCR protocol detected cervical *Chlamydia trachomatis* in the urine samples as effectively as culture detected cervical *Chlamydia trachomatis* in the cervical swabs. Moreover, the LCR protocol was more effective at detecting *Chlamydia trachomatis* of cervical or urethral origin in urine than the culture and EIA methods combined. The EIA results raise the possibility that 10 of the 15 women that were positive by culture may have had a dual cervical and urethral infection. Accordingly, the LCR protocol may have been detecting urethral *Chlamydia trachomatis* in the urine samples taken from these 10 women. However, the EIA results also suggest that 5 of the women were infected only in the cervix and the LCR protocol yielded positive results for these women.

The forgoing examples are presented by way of illustration and are not intended to limit the scope of the invention as set forth in the appended claims. Additionally, all patents and publications mentioned above are herein incorporated by reference.

What is claimed is:

1. A method of detecting cervical *Chlamydia trachomatis* comprising the steps of:
    (a) contacting a female urine sample suspected of containing *Chlamydia trachomatis* nucleic acid originating from the cervix with nucleic acid amplification reagents to form a reaction mixture;
    (b) placing said reaction mixture under hybridization and amplification conditions to produce at least one copy of a *Chlamydia trachomatis* target sequence wherein said *Chlamydia trachomatis* nucleic acid comprises said *Chlamydia trachomatis* target sequence; and
    (c) detecting said at least one copy of said target sequence as an indication of the presence of cervical *Chlamydia trachomatis*.

2. The method of claim 1 wherein said urine sample is collected from the first 40 mL of a female urine stream.

3. The method of claim 1 wherein said amplification reagents comprise:
    (a) an enzyme having polymerase activity;

(b) one or more deoxynucleotide triphosphates; and (c) at least two oligonucleotide probes.

4. The method of claim 1 further comprising the steps of:

(a) separating *Chlamydia trachomatis* cells from said urine sample, and (b) lysing said *Chlamydia trachomatis* cells, wherein said separating and said lysing occur prior to contacting said urine sample with said amplification reagents.

5. A method of simultaneously detecting cervical and urethral *Chlamydia trachomatis* comprising the steps of:

(a) contacting a female urine sample suspected of containing *Chlamydia trachomatis* nucleic acid originating from the cervix and urethra with nucleic acid amplification reagents to form a reaction mixture;

(b) placing said reaction mixture under hybridization and amplification conditions to produce at least one copy of a *Chlamydia trachomatis* target sequence wherein said *Chlamydia trachomatis* nucleic acid comprises said *Chlamydia trachomatis* target sequence; and (c) detecting said at least one copy of said target sequence as an indication of the presence of cervical and urethral *Chlamydia trachomatis*.

6. The method of claim 5 wherein said urine sample is collected from the first 40 mL of a female urine stream.

7. The method of claim 5 wherein said amplification reagents comprise:

(a) an enzyme having polymerase activity; and (b) one or more deoxynucleotide triphosphates; and (d) at least two oligonucleotide probes.

8. The method of claim 5 further comprising the steps of:

(a) separating *Chlamydia trachomatis* cells from said urine sample, and (b) lysing said *Chlamydia trachomatis* cells, wherein said separating and said lysing occur prior to contacting said urine sample with said amplification reagents.

* * * * *

SEQUENCE LISTING (1) GENERAL INFORMATION:

(iii) NUMBER OF SEQUENCES: 25

(2) INFORMATION FOR SEQ ID NO:1:

```
    (i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis (xi) SEQUENCE DESCRIPTION: SEQ ID NO:1:

GCTTTGAGTT CTGCTTCCTC CTTGCAAGCT CTGCCTGTGG GGAATCCT            48

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:2:

GCTTTGAGTT CTGCTTCCTC CTTG                                     24

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:3:

GGAGGAAGCA GAACTCAAAG C                                        21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:4:

GCTCTGCCTG TGGGGAATCC T                                        21

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:5:

AGGATTGCCC ACAGGCAGAG CTTG                                     24

(2) INFORMATION FOR SEQ ID NO:6:

(i) SEQUENCE CHARACTERISTICS:
        (A) LENGTH: 48 base pairs
```

(B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis (xi) SEQUENCE DESCRIPTION: SEQ ID NO:6:

TTGGGATCGT TTTGATGTAT TCTGTACATT AGGAGCCACC AGTGGATA                48

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:7:

TTGGGATCGT TTTGATGTAT TCTGT                                        25

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:8:

GAATACATCA AAACGATCCC AA                                           22

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:9:

TTAGGAGCCA CCAGTGGATA                                              20

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:10:

TATCCACTGG TGGCTCCTAA TGT                                          23

(2) INFORMATION FOR SEQ ID NO:11:

(i) SEQUENCE CHARACTERISTICS:
        (A) LENGTH: 46 base pairs
        (B) TYPE: nucleic acid
        (C) STRANDEDNESS: double (D) TOPOLOGY: linear (ii) MOLECULE TYPE: DNA (genomic)

(vi) ORIGINAL SOURCE:
          (A) ORGANISM: Chlamydia trachomatis (xi) SEQUENCE DESCRIPTION: SEQ ID NO:11:

TGGATGCAGA CAAATACGCA GTTACAGTTG AGACTCGCTT GATCGA                46

(2) INFORMATION FOR SEQ ID NO:12:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE:  DNA (synthetic)

(xi) SEQUENCE DESCRIPTION: SEQ ID NO:12:

TGGATGCAGA CAAATACGCA GTT                                        23

(2) INFORMATION FOR SEQ ID NO:13:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE:  DNA (synthetic)

(xi) SEQUENCE DESCRIPTION: SEQ ID NO:13:

TGCGTATTTG TCTGCATCCA                                            20

(2) INFORMATION FOR SEQ ID NO:14:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE:  DNA (synthetic)

(xi) SEQUENCE DESCRIPTION: SEQ ID NO:14:

GTTGAGACTC GCTTGATCGA                                            20

(2) INFORMATION FOR SEQ ID NO:15:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE:  DNA (synthetic)

(xi) SEQUENCE DESCRIPTION: SEQ ID NO:15:

TCGATCAAGC GAGTCTCAAC TGT                                        23

(2) INFORMATION FOR SEQ ID NO:16:

(i) SEQUENCE CHARACTERISTICS:
          (A) LENGTH: 48 base pairs
          (B) TYPE: nucleic acid
          (C) STRANDEDNESS: double
          (D) TOPOLOGY: linear (ii) MOLECULE TYPE: DNA (extrachromosomal)

(vi) ORIGINAL SOURCE:
             (A) ORGANISM: Chlamydia trachomatis (xi) SEQUENCE DESCRIPTION: SEQ ID NO:16:

GACTTTGCAA CTCTTGGTGG TAGACTTGGT CATAATGGAC TTTTGTTG                48

(2) INFORMATION FOR SEQ ID NO:17:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE:  DNA (synthetic)

(xi) SEQUENCE DESCRIPTION: SEQ ID NO:17:

GACTTTGCAA CTCTTGGTGG TAGA                                          24

(2) INFORMATION FOR SEQ ID NO:18:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE:  DNA (synthetic)

(xi) SEQUENCE DESCRIPTION: SEQ ID NO:18:

ACCACCAAGA GTTGCAAAGT C                                             21

(2) INFORMATION FOR SEQ ID NO:19:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE:  DNA (synthetic)

(xi) SEQUENCE DESCRIPTION: SEQ ID NO:19:

GGTCATAATG GACTTTTGTT G                                             21

(2) INFORMATION FOR SEQ ID NO:20:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE:  DNA (synthetic)

(xi) SEQUENCE DESCRIPTION: SEQ ID NO:20:

CAACAAAAGT CCATTATGAC CAAG                                          24

(2) INFORMATION FOR SEQ ID NO:21:

(i) SEQUENCE CHARACTERISTICS:
             (A) LENGTH: 54 base pairs
             (B) TYPE: nucleic acid
             (C) STRANDEDNESS: double
             (D) TOPOLOGY: linear (ii) MOLECULE TYPE: DNA (extrachromosomal)

-continued

```
    (vi) ORIGINAL SOURCE:
        (A) ORGANISM: Chlamydia trachomatis (xi) SEQUENCE DESCRIPTION: SEQ ID NO:21:

ATTTTAAGAA GACGCTTCCT TCCATTGAAC TATTCTCAGC AACTTTGAAT TCTG          54

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE:  DNA (synthetic)

(xi) SEQUENCE DESCRIPTION: SEQ ID NO:22:

ATTTTAAGAA GACGCTTCCT TCCATTG                                        27

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:23:

TGGAAGGAAG CGTCTTCTTA AAAT                                           24

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: circular (ii) MOLECULE TYPE:  DNA (synthetic)

(xi) SEQUENCE DESCRIPTION: SEQ ID NO:24:

TATTCTCAGC AACTTTGAAT TCTG                                           24

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE:  DNA (synthetic)

(xi) SEQUENCE DESCRIPTION: SEQ ID NO:25:

CAGAATTCAA AGTTGCTGAG AATAGTT                                        27
```